United States Patent [19]

Raible et al.

[11] 4,292,969
[45] Oct. 6, 1981

[54] FLUID REGULATING DEVICE WITH TORSIONAL CONTROL

[76] Inventors: Donald A. Raible, 1262 Camden Dr., Santa Ana, Calif. 92705; Stuart M. Poticha, 2800 N. Lake Shore Dr., Apt. 2216, Chicago, Ill. 60613; Rita Stauffer, 1016 W. Hollywood, Chicago, Ill. 60660

[21] Appl. No.: 105,028

[22] Filed: Dec. 19, 1979

[51] Int. Cl.³ .................. A61M 5/00; E16L 55/14
[52] U.S. Cl. ................... 128/214 R; 251/4; 251/340
[58] Field of Search ............ 128/214 R, 214 C, 227, 128/274; 251/4, 341, 342, 348; 222/444

[56] References Cited

U.S. PATENT DOCUMENTS

| | | |
|---|---|---|
| 715,429 | 12/1902 | Seabury . |
| 2,314,767 | 3/1943 | Burrell . |
| 2,416,391 | 2/1947 | Hixon ........................... 251/4 X |
| 2,844,351 | 7/1958 | Smith ......................... 128/214 R |
| 2,908,476 | 10/1959 | Hidding . |
| 2,935,088 | 5/1960 | Thompson et al. . |
| 3,042,067 | 7/1962 | Hidding . |
| 3,167,085 | 1/1965 | Redmer . |
| 3,329,390 | 7/1967 | Hulsey ............................. 251/4 |
| 3,332,439 | 7/1967 | Burke . |
| 3,497,175 | 2/1970 | Koland . |
| 3,515,170 | 6/1970 | Mullaly . |
| 3,625,211 | 12/1971 | Butler . |
| 3,774,603 | 11/1973 | McPhee . |
| 3,776,229 | 12/1973 | McPhee . |
| 3,844,283 | 10/1974 | Dabney . |
| 3,871,229 | 3/1975 | Fletcher . |
| 3,931,818 | 1/1976 | Goldowsky . |
| 3,982,724 | 9/1976 | Citrin . |

*Primary Examiner*—Stephen C. Pellegrino
*Attorney, Agent, or Firm*—Allegretti, Newitt, Witcoff & McAndrews

[57] ABSTRACT

An improved fluid regulating device is used in a parenteral administration system having tubing. The device provides torsional flexure of the tubing by relative rotation between first and second body members to regulate fluid flow.

10 Claims, 15 Drawing Figures

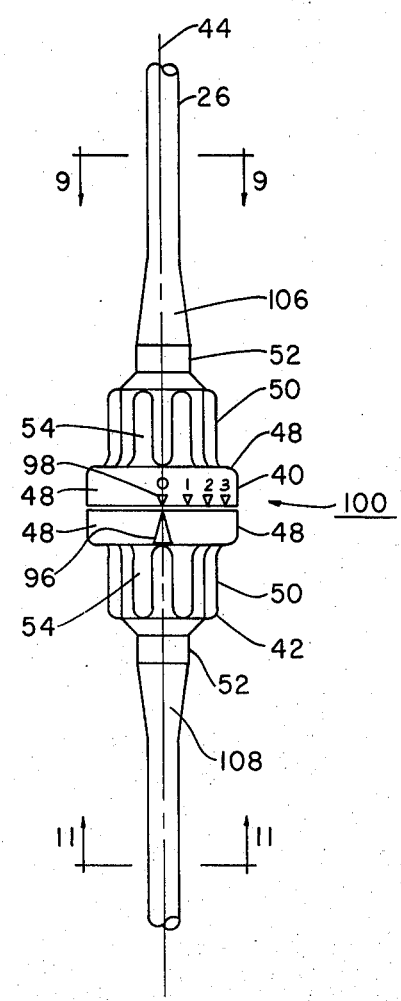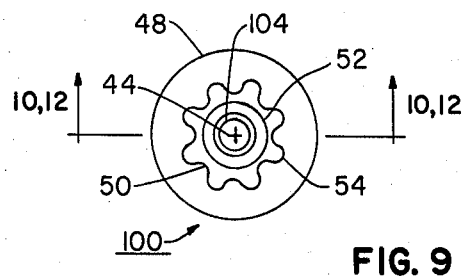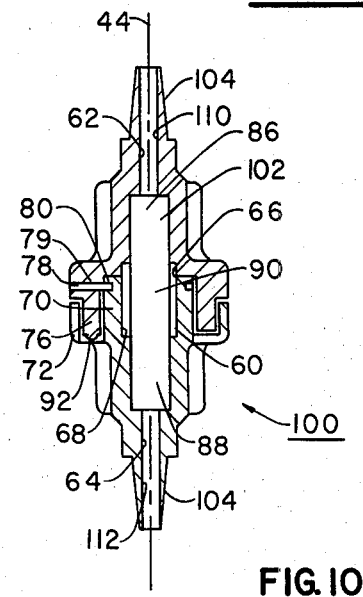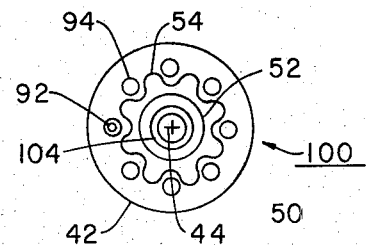
FIG. 8
FIG. 9
FIG. 10
FIG. 11

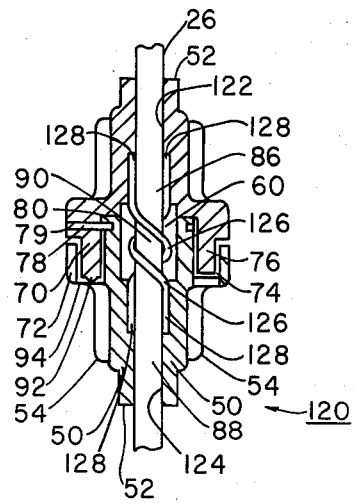
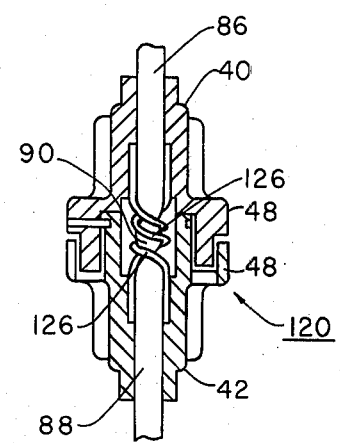
FIG. 13
FIG. 14
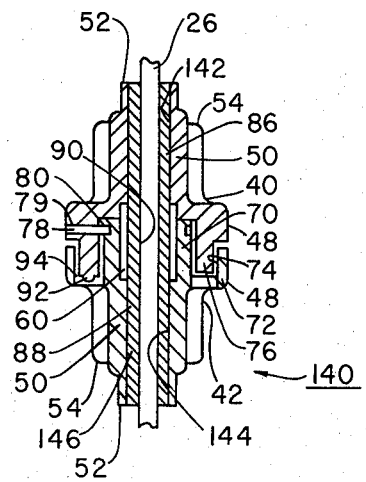
FIG. 15

FLUID REGULATING DEVICE WITH TORSIONAL CONTROL

BACKGROUND OF THE INVENTION

This invention relates to parenteral administrations systems and fluid regulating devices, and most particularly, to an improved fluid regulating device for use in a parenteral administration system.

Parentral administration systems are utilized to transfer intravenous solutions to medical patients. Such systems typically include a fluid supply container, a parentral needle and tubing interconnecting the fluid supply container with the needle. Transfer of the solution is achieved through gravity by suspension of the container above the patient.

A significant problem in the utilization of parentral administration systems is the regulation of the flow of solution to the patient. This problem has along been known, and has resulted in a variety of fluid regulating devices. As an example, roller clamps have been attached to variably compress the tubing and thereby provide a variable rate of flow. Generally, these devices all control fluid flow in the manner of roller clamps, i.e., by pinching force on the tubing. While a few of these devices have proved highly useful, most are cumbersome, inaccurate, incapable of rapid variation or hazardous. No one device fully satisfies long-felt needs for such devices.

A principal reason for the inadequacies of these devices is that the pinching of typical tubing results in deformation without reduction of the cross-sectional area of the internal passageway, until the tubing is almost totally collapsed. As a result, fluid flow varies from substantially full flow to zero flow over a minute range of deformation near total tubing collapse. Truly accurate control of deformation in this range is extremely difficult. Another reason for the inadequacies of prior art devices is that typical tubing is not satisfactorily resilient when pinched. As a result, accurate variation of fluid flow through the tubing from a preselected flow to a desired flow is also difficult, if not impossible.

SUMMARY OF THE INVENTION

It is thus an object of the present invention to provide an improved fluid regulating device.

Another object of the present invention is to provide an improved fluid regulating device for use in a parenteral administration system having a fluid supply container, a parenteral needle and tubing.

Another object of the present invention is to provide an improved fluid regulating device for use in a parenteral administration system which provides accurate and reproducable fluid flow rates.

Another object of the present invention is to provide an improved fluid regulating device for use in a parenteral administration system which co-operates with the tubing typically utilized in parenteral administration systems.

Another object of the present invention is to provide an improved fluid regulating device for use in a parenteral administration system which, in at least one embodiment, does not interrupt the tubing or otherwise compromise the internal sterility thereof.

Another object of the present invention is to provide an improved fluid regulating device for use in a parenteral administration system that is streamlined and economical of manufacture.

Thus, in a principal aspect, the present invention is an improved fluid regulating device for use in a parenteral administration system having a fluid supply container, a parenteral needle and torsionally flexible tubing. The device comprises a first body member, first securing means, a second body member, second securing means, and mounting means. The first body member has a first channel wall and a first chamber wall. The first channel well defines a first channel for a first tubing portion of flexible tubing and the first chamber wall defines a first open-ended portion of a chamber along the first channel. The first chamber wall has a minimum diametric dimension greater than the maximum outer dimension of the flexible tubing. The first securing means is on the first body member for securing the first body member to the first tubing portion for common rotation about a first axis through the chamber.

The second body member has a second channel wall and a second chamber wall. The second channel wall defines a second channel for a second tubing portion of flexible tubing, and the second chamber wall defines a second openended portion of the chamber along the second channel. The second chamber wall has a minimum diametric dimension greater than the maximum outer dimension of the flexible tubing. The second securing means is on the second body member for securing the second body member to the second tubular portion of flexible tubing for common rotation about a second axis through the chamber.

The mounting means is on the first body member and the second body member. The mounting means mounts the first body member to the second body member with the axes coincident and the first portion of the chamber open to the second portion of the chamber. The mounting means provides for relative rotation of the body members about the axes. With the two body members thus mounted, an unsecured portion of flexible tubing that is intermediate and joined to the first and second tubing portions passes through the chamber.

The first body member is rotatable relative to the second body member between a first relative rotational position and a second relative rotational position. In the first relative rotational position, the unsecured tubing portion is in a first condition of torsional flexure. In the second relative rotational position, the unsecured tubing portion is in a second condition of torsional flexure. Thus, the flexible tubing is torsionally flexed by relative rotation of the first and second body members so as to regulate the fluid flow therethrough.

As should now be understood, the improved fluid regulating device of the present invention co-operates with and may have as an element thereof torsionally flexible tubing. It has been discovered through this invention that the tubing typically used in parenteral administration systems is torsionally flexible, such that torsional flexure of the tubing provides significantly improved characteristics of fluid flow variation. Flow varies in the tubing substantially uniformly over a broad range of torsional flexure, and the tubing is significantly more resilient to torsional flexure than pinching. Thus, it is believed that the present invention is a significant advance in the art of fluid regulating devices, specifically those for parenteral administration systems. For a more thorough understanding of the present invention, attention is directed to the four preferred embodiments disclosed herein.

BRIEF DESCRIPTION OF THE DRAWINGS

In the detailed description which follows, four preferred embodiments of the present invention are described in relation to the accompanying drawing, which consists of fifteen figures. The first preferred embodiment is illustrated in FIGS. 1-7, the second in FIGS. 8-12, the third in FIGS. 13-14, and the fourth in FIG. 15. These fifteen figures are briefly described as follows:

FIG. 8 is an elevational view of the second preferred embodiment of the present invention in situ;

FIG. 9 is a top plan view of the second preferred embodiment of the present invention, taken along line 9—9 of FIG. 8;

FIG. 10 is a cross-sectional view of the second preferred embodiment of the present invention, similar to FIG. 5, taken along line 10—10 of FIG. 9;

FIG. 11 is a bottom plan view of the second preferred embodiment of the present invention, taken along line 11—11 of FIG. 8;

FIG. 13 is a cross-sectional view of the third preferred embodiment of the present invention, similar to FIGS. 6 and 11;

FIG. 14 is a cross-sectional view of the third preferred embodiment of the present invention, similar to FIGS. 7 and 12; and FIG. 15 is a cross-sectional view of the fourth preferred embodiment of the present invention, similar to FIGS. 5, 10 and 13.

In the drawing and the detailed description of the four preferred embodiments which follows, like reference numerals refer to like components of the four embodiments.

DETAILED DESCRIPTION OF THE PREFERRED EMBODIMENTS

Figure 1:
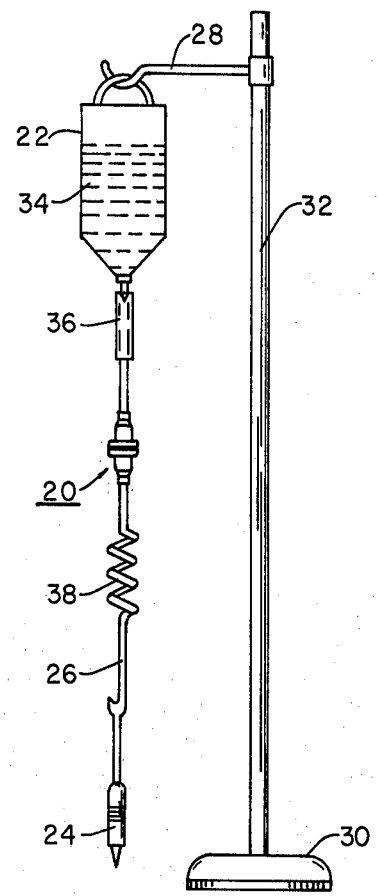
FIG. 1 is an elevational view of a complete parenteral administration system incorporating the first preferred embodiment of the present invention.

Referring to FIG. 1 of the accompanying drawing, the first preferred embodiment of the present invention is a fluid regulating device 20 for use in a parenteral administration system having a fluid supply container 22, a parenteral needle 24 and flexible tubing 26. The device 20 in situ is positioned along the flexible tubing 26 intermediate or between the fluid supply container 22 and the needle 24. In use, the supply container 22, which may be a bottle or bag or the like, is suspended from a fixture such as a hook 28, which is shown supported by a stand having a base 30 and a supporting column 32. The container 22 contains a fluid parenteral solution 34 intended for a medical patient (not shown). The container 22 feeds the solution 34 by gravity to a conventional drip chamber 36 and into the flexible tubing 26. The solution 34 passes through the flexible tubing 26, including an extensible and retractable coil 38 thereof, to the needle 24. The needle 24 is introduced into the body of the patient as by insertion into a vein, and the solution 34 is thereby administered to the patient. It should be understood that this parenteral administration system is described for environmental purposes only, and that the second, third and fourth preferred embodiments of the present invention are utilized as is the first.

Figure 2:
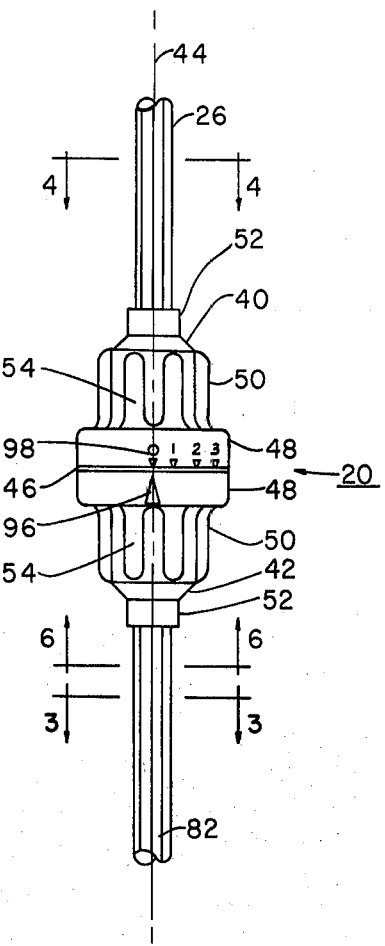
FIG. 2 is an elevational view of the first preferred embodiment of the present invention in situ.

Referring to FIG. 2, the device 20 includes a first body member 40 and a second body member 42. While orientation of the device 20 does not affect its operation, the first body member 40 is shown in FIG. 2 mounted atop the second body member 42. The body members 40, 42 are aligned along a vertical axis 44 about a horizontal midline 46. This orientation is typical when the device 20 is in position for usage.

Figure 4:
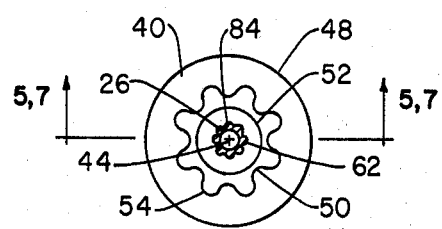
FIG. 4 is a top plan view of the first preferred embodiment of the present invention, taken along line 4—4 of FIG. 2.
Figure 6:
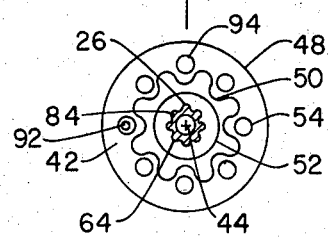
FIG. 6 is a bottom plan view of the first preferred embodiment of the present invention, taken along line 6—6 of FIG. 2.

Each body member 40, 42 includes an indicator portion 48, a handle portion 50 and a tube receiving portion 52. The indicator portions 48 are adjacent the midline 46. The handle portions 50 are adjacent the indicator portions 48, opposite each other about the midline 46. The tube receiving portions 52 are also opposite each other about the midline 46, and adjacent the handle portions 50. As shown in FIGS. 4 and 6, portions 48, 52 are generally cylindrical about the axis 44, while the handle portions 50 include axially extending ribs 54 about their circumferences. The portions 52 have a diameter greater than but substantially comparable to the mean diameter of the tubing 26, the portions 50 have a minimum diametric dimension greater than the diameter of the portions 52 and the portions 48 have a diameter greater than the maximum diametric dimension of the portions 50. As most preferred, the body members 40, 42 are molded of plastic.

Figure 5:
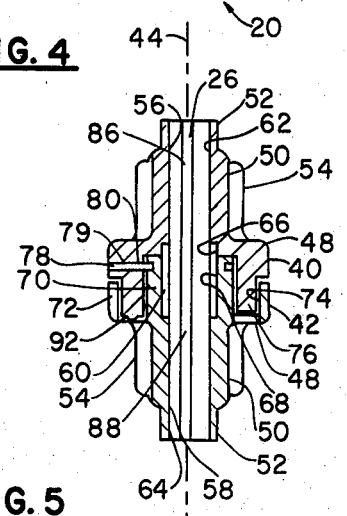
FIG. 5 is a cross-sectional view of the first preferred embodiment in situ, with the tubing fully open for maximum infusion rate, taken along line 5—5 of FIG. 4.

Referring to FIG. 5, the first body member 40 defines a first channel 56 for tubing 26, the second body member 42 defines a second channel 58 for tubing 26 and the body member 40, 42 together define a chamber 60. The channels 56, 58 and the chambers 60 are generally cylindrical and aligned along the axis 44. The first channel 56 is defined by a first channel wall 62 of the first body member 40. The second channel 58 is defined by a second channel wall 64 of the second body member 42. The chamber 60 is defined by a first chamber wall 66 of the first body member 40 and a second chamber wall 68 of the second body member 42. The chamber 60 is intermediate the first channel 56 and the second channel 58, with the first chamber wall 66 defining the upper portion of the chamber 60 and the second chamber wall 68 defining the lower portion thereof.

The first body member 40 is mounted atop the second body member 42 for relative rotation therebetween about the axis 44. The second chamber wall 68 defines an upstanding, internal flange 70 within the indicator portion 48 of the second body member 42. An upstanding, external flange 72 extends about the periphery of the indicator portion 48 of the second body member 42. The flanges 70, 72 are cylindrical and define an annular recess 74 between the flanges 70, 72. A mating flange 76 extends downward from the indicator portion 48 of the first body member 40 into the recess 74. Relative rotation of the body members 40, 42 occurs by rotational sliding movement of the mating flange 76 in the recess 74. A retainer ring 78 extends through a first groove 79 in the indicator portion 48 of the first body member 40 into a second groove 80 in the internal flange 70. The retainer ring 78 retains the mating flange 76 in the recess 74 and prevents axial movement between the body members 40, 42.

Figure 3:
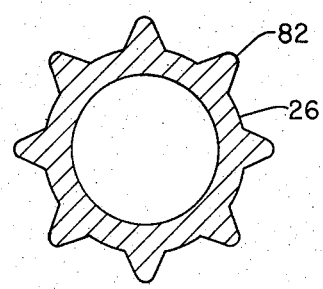
FIG. 3 is a cross-sectional view of the tubing of the parenteral administration system of FIG. 1, taken along line 3—3 of FIG. 2.

The first body member 40 is secured to the tubing 26 along the first channel 56, and the second body member 42 is secured to the tubing 26 along the second channel 58. As shown best in FIG. 3, the tubing 26 has a plurality of radially outwardly extending ribs or fins 82 in at least the area of the device 20. Referring to FIGS. 4 and 6, the first and second channel walls 62, 64 include axially extending, radially inwardly extending mating ribs 84 that mate with the ribs 82. The ribs 82, 84 mate loosely such that the device 20 is axially moveable relative to the tubing 26 while the body members 40, 42 are secured for common rotation about the axis 44 with the flexible tubing 26. That is, the device 20 is slidable along the tubing 26, while rotation of the body member 40, 42 causes rotation of adjacent portions of the tubing 26. Specifically, and with reference to FIG. 7, rotation of the fist body member 40 causes rotation of a first tubing portion 86 of the tubing 26 defined along the first channel 56; rotation of the second body member 42 causes rotation of a second tubing portion 88 of the tubing 26 defined along the second channel 58.

Figure 7:
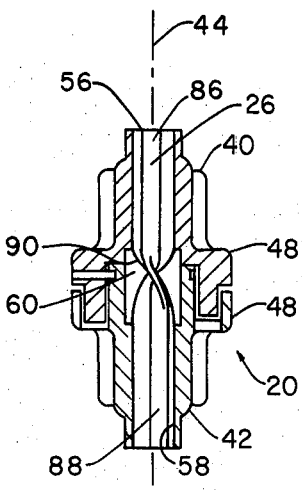
FIG. 7 is a cross-sectional view of the first preferred embodiment in situ, with the tubing torsionally adjusted for a reduced infusion rate, taken along line 7—7 of FIG. 4.

As should now be apparent, relative rotation between the body members 40, 42 causes relative rotation between the tubing portions 86, 88. Because the tubing portions 86, 88 are joined to each other by a tubing portion 90 within the chamber 60, and because the tubing portion 90 is unsecured, relative rotation between the tubing portions 86, 88 results in torsional flexure or twisting of the unsecured tubing portion 90, as shown in FIG. 7.

The torsional flexure of the unsecured tubing portion 90 constricts the internal passageway in the tubing portion 90, thereby resulting in reduced fluid flow through the tubing 26. Increased and decreased torsional flexure of the unsecured tubing portion 90 results in increased and decreased fluid flow therethrough, respectively. Thus, fluid flow is dependent on torsional flexure and the relative rotation between the body members 40, 42. Calibration of the relative rotation of the body members 40, 42 provides for the selection of fluid flow by the selection of a relative rotational position.

Maintenance of the relative rotational position of the body members 40, 42 causes a constant flow through the device 20. As shown in FIGS. 5 and 6, the first body member 40 includes a detent 92 along the bottom of the flange 76. The detent 92 has a hemispherical shape and cooperates with detent openings 94 in the second body member 42. The detent openings 94 are best seen in FIG. 6, where only one detent opening is referenced, for clarity. The detent openings 94 are defined in the recess 74 of the second body member 42. As formed of plastic, the body members 40, 42 are flexible to provide for movement of the detent 92 from detent opening 94 to detent opening 94. If the body members 40, 42 are formed of non-flexible material, the detent 92 is made spherical and biased toward the detent openings 94 by a spring set within a recess in the flange 76.

Placement of the detent openings 94 determines the calibration of the body member 40, 42. Movement of the detent 92 from one detent opening 94 to an adjacent detent opening 94 causes an incremental change in fluid flow rate. As shown in FIG. 2, the position of the detent 92 is indicated on the indicator portions 48 by a marker 96 and markings 98.

Figure 12:
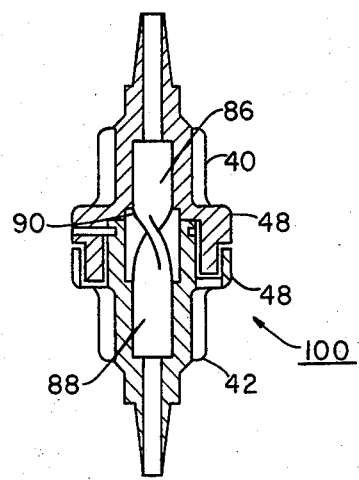
FIG. 12 is a cross-sectional view of the second preferred embodiment of the present invention similar to FIG. 7, taken along line 12—12 of FIG. 9.

Referring now to FIGS. 8-11, the second preferred embodiment of the present invention is a device 100. As shown and indicated by like reference numerals, the device 100 is substantially similar to the device 20. Significant differences include the provision of a captive tubing segment 102 and tapered tips 104 on the tube receiving portions 52. The captive tubing segment 102 and the tips 104 permit the placement of the device 100 in a length of smooth-wall tubing 26 that has been previously connected with a needle 24 and container 22. The tubing 26 is cut between the container 22 and the needle 24 to provide free ends 106, 108. The end 106 is placed over the tip 104 of the first body member 40 and the end 108 is placed over the tip 104 of the second body member 42. The ends 106, 108 are clamped or glued in position, or as shown in FIG. 8, held in position under the tension of diametric expansion. The channels 110, 112 of the device 100 have a diameter along the tips 104 substantially equal to the normal inner diameter of the tubing 26. Adjacent the chamber 60, the channels 110, 112 are enlarged to accomodate the captive tubing segment 102. The segment 102 is captive in the sense that assemblage of the device 100 involves the non-removable placement of the segment 102 within the enlarged portions of the channels 110, 112 and the chamber 60. The first tubing portion 86, the second tubing portion 88 and the unsecured tubing portion 90 are defined within the captive tubing segment 102. Thus, the device 100 provides fluid flow regulation substantially like the device 20, as shown in FIGS. 10 and 12.

Referring to FIGS. 13-14, the third preferred embodiment of the present invention is a device 120. In the device 120, the tubing 26 and channels 122, 124 have smooth cylindrical surfaces or walls. Common rotation of the tubing portions 86, 88 with the body member 40, 42 and thus, torsional flexion of the tubing 26, is provided by loosely coiled helical springs 126. The springs 126 are positioned within the chamber 60 about the tubing 26 with ends 128 embedded within the body members 40, 42. Relative rotation of the body member 40, 42 causes torsional flexure of the springs 126, which by friction against the tubing 26 causes torsional flexure thereof.

Referring to FIG. 15, the fourth preferred embodiment of the present invention is a device 140. The channels 142, 144 are enlarged to accomodate a tubing segment 146 separate from the tubing 26. The tubing segment 144 has an inner diameter greater than the outer diameter of the tubing 26, and the tubing 26, tubing segment 146 and channels 142, 144 have smooth cylindrical surfaces. The first tubing portion 86, the second tubing portion 88 and the unsecured tubing portion 90 are defined within the tubing segment 146. The tubing 26 is inserted through the tubing segment 146. The first body member 40 is secured to the first tubing portion 86 by chemically reactive glue or the like, and the second body member 42 is similarly secured to the second tubing portion 88. Rotation of the body members 40, 42 causes torsional flexure of the tubing segment 146 and thereby the flexible tubing 26.

Each of the four preferred embodiments of the present invention has significant advantages. The first embodiment is movable along the ribbed portion of the tubing 26 to any desired position and need not be sterile, since the interior of the tubing 26 does not contact any part of the device 20. The second preferred embodiment can be spliced into a previously assembled parenteral administration system and no risk of inaccurate fluid flow is caused by any possible abberation in the torsional flexure characteristics of the tubing 26 previously chosen for the system. Neither the third preferred embodiment nor the fourth preferred embodiment need be sterile, and each is useful with standard smoothwall intravenous tubing. Each is movable along the tubing like the first preferred embodiment, and each has the accuracy advantage of the second preferred embodiment. At present, the third preferred embodiment is most preferred, because of its extreme accuracy.

A highly important invention to the art of fluid regulating devices for parenteral administration systems has now been described. To particularly point out and distinctly claim the subject matter regarded as invention, the following claims conclude this specification. Except as set forth in the claims, or as corresponding to elements set forth in the claims, the details of the four preferred embodiments of the present invention are illustrative and not restrictive. All devices, which though varied in detail, come within the proper scope of the claims are intended to be embraced therein.

What is claimed is:

1. An improved fluid regulating device for use in a parenteral administration system having a fluid supply container, a parenteral needle and torsionally flexible tubing, comprising:

a first body member having a first channel wall and a first chamber wall, the first channel wall defining a first channel for a first tubing portion of flexible tubing and the first chamber wall defining a first open-ended portion of a chamber along the first channel, the first chamber wall having a minimum diametric dimension greater than the maximum outer dimension of the flexible tubing;

first securing means on the first body member for securing the first body member to the first tubing portion for common rotation about a first axis through the chamber;

a second body member having a second channel wall and a second chamber wall, the second channel wall defining a second channel for a second tubing portion of the flexible tubing and the second chamber wall defining a second open-ended portion of the chamber along the second channel, the second chamber wall having a minimum diametric dimension greater than the maximum outer dimension of the flexible tubing;

second securing means on the first body member for securing the second body member to the second tubular portion for common rotation about a second axis through the chamber;

mounting means on the first body member and the second body member for mounting the first body member to the second body member with the axes coincident for rotation about the axes, and with the first portion of the chamber open to the second portion of the chamber such that an unsecured portion of flexible tubing that is intermediate and jointed to the first tubing portion and the second tubing portion passes through the chamber, and with the first body member being rotatable relative to the second body member such that in a first relative rotational position, the unsecured tubing portion is in a first condition of torsional flexure and in a second relative rotational position, the unsecured tubing portion is in a second condition of torsional flexure;

whereby the unsecured portion of the flexible tubing is torsionally flexed by relative rotation of the first and second body member so as to regulate fluid flow therethrough.

2. An improved fluid regulating device for use with torsionally flexible tubing, comprising:

a first body member having a first channel wall and a first chamber wall, the first channel wall defining a first channel for a first tubing portion of flexible tubing and the first chamber wall definig a first open-ended portion of a chamber along the first channel, the first chamber wall having a minimum diametric dimension greater than the maximum outer dimension of the flexible tubing;

first securing means on the first body member for securing the first body member to the first tubing portion for common rotation about a first axis through the chamber;

a second body member having a second channel wall and a second chamber wall, the second channel wall defining a second channel for a second tubing portion of the flexible tubing and the second chamber wall defining a second open-ended portion of the chamber along the second channel, the second chamber wall having a minimum diametric dimension greater than the maximum outer dimension of the flexible tubing;

second securing means on the first body member for securing the second body member to the second tubular portion for common rotation about a second axis through the chamber;

mounting means on the first body member and the second body member for mounting the first body member to the second body member with the axes coincident for rotation about the axes, and with the first portion of the chamber open to the second portion of the chamber such that an unsecured portion of flexible tubing that is intermediate and jointed to the first tubing portion and the second tubing portion passes through the chamber, and with the first body member being rotatable relative to the second body member such that in a first relative rotational position, the unsecured tubing portion is in a first condition of torsional flexure and in a second relative rotational position, the unsecured tubing portion is in a second condition of torsional flexure;

whereby the unsecured portion of the flexible tubing is torsionally flexed by relative rotation of the first and second body member so as to regulate fluid flow therethrough.

3. An improved fluid regulating device as in claim 1 or 2 further comprising means on the first body member and the second body member in the second body member for releasably maintaining the first body member in the first and second rotational positions.

4. An improved fluid regulating device as in claim 1 or 2 further comprising said flexible tubing including outwardly extending ribs therealong, in which the first securing means and the second securing means include inwardly extending ribs formed along the first and second channel walls which mate with the outwardly extending ribs to provide for said common rotation.

5. An improved fluid regulating device as in claim 4 wherein the inwardly extending ribs mate loosely with the outwardly extending ribs to provide for movement of the fluid regulating device along the flexible tubing.

6. An improved fluid regulating device as in claim 1 or 2 in which the flexible tubing includes physically separate first, second and third tubing segments, the first tubing portion, the second tubing portion and the unsecured tubing portion being formed in the third segment of the tubing, in which the first body member includes a first fitting for attachment of the first tubing segment, and in which the second body member includes a second fitting for attachment of the second tubing segment.

7. An improved fluid regulating device as in claim 6 in which the first and second fittings are tapered for insertion within the first and second tubing segments, respectively.

8. An improved fluid regulating device as in claim 1 or 2 in which the first tubing portion is attached to the first body member and the second tubing portion is attached to the second body member.

9. An improved fluid regulating device as in claim 1 or 2 in which the flexible tubing includes a first tubing segment having a first outer diameter and a second tubing segment having an inner diameter greater than the first outer diameter, the first, second and third tubing portions being formed in the second segment of tubing, in which the first and second channel walls have minimum diametric dimensions greater than the outer diameter of the first segment of tubing, and in which the first and second chamber walls have a minimum diametric dimension greater than the outer diameter of the second tubing segment, whereby the first tubing segment is inserted through the second tubing segment and flexure of the second tubing segment causes flexure of the first tubing segment.

10. An improved fluid regulating device is in claim 1 or 2 further comprising a helical spring positioned generally within the chamber about the unsecured tubing portion and having ends attached to the first and second body members, whereby relative rotation of the first and second body members causes torsional flexure of the spring and thereby the unsecured tubing portion.

* * * * *

UNITED STATES PATENT AND TRADEMARK OFFICE
CERTIFICATE OF CORRECTION

PATENT NO. : 4,292,969

DATED : October 6, 1981

INVENTOR(S) : Donald A. Raible, et al.

It is certified that error appears in the above—identified patent and that said Letters Patent is hereby corrected as shown below:

Col. 7, line 36          Change "channel", should be --chamber--.

Signed and Sealed this

Nineteenth Day of January 1982

[SEAL]

Attest:

Attesting Officer

GERALD J. MOSSINGHOFF

Commissioner of Patents and Trademarks